United States Patent [19]
Silverman

[11] Patent Number: 5,464,422
[45] Date of Patent: Nov. 7, 1995

[54] SUTURE NEEDLE

[75] Inventor: James D. Silverman, Flagstaff, Ariz.

[73] Assignee: W. L. Gore & Associates, Inc., Newark, Del.

[21] Appl. No.: 374,383

[22] Filed: Jan. 11, 1995

Related U.S. Application Data

[63] Continuation of Ser. No. 86,500, Jul. 1, 1993, abandoned.

[51] Int. Cl.⁶ .................................................. A61B 17/04
[52] U.S. Cl. ........................................ 606/223; 606/222
[58] Field of Search ................................ 606/222–223; 223/102; 163/5

[56] References Cited

U.S. PATENT DOCUMENTS

| | | | |
|---|---|---|---|
| 1,599,059 | 1/1926 | Morton | 606/223 |
| 2,841,150 | 7/1958 | Riall | 606/223 |
| 2,869,550 | 1/1959 | Kurtz | 606/222 |
| 3,038,475 | 6/1962 | Orcutt | 606/222 |
| 3,094,123 | 6/1963 | Kurtz | 606/223 |
| 3,265,070 | 8/1966 | Kurtz | 606/223 |
| 3,636,955 | 1/1972 | Kurtz | 606/223 |
| 4,128,351 | 12/1978 | Kurtz et al. | 606/223 |
| 4,513,747 | 4/1985 | Smith | 606/223 |
| 4,799,484 | 1/1989 | Smith et al. | 606/223 |
| 4,932,961 | 6/1990 | Wong et al. | 606/223 |
| 5,123,910 | 6/1992 | McIntosh | 606/223 |
| 5,178,628 | 1/1993 | Otsuka et al. | 606/222 |

FOREIGN PATENT DOCUMENTS

| | | |
|---|---|---|
| 0224117 | 6/1987 | European Pat. Off. |
| 0286438 | 10/1988 | European Pat. Off. |
| 0413862 | 2/1991 | European Pat. Off. |
| 0453132 | 10/1991 | European Pat. Off. |
| 2657247 | 7/1991 | France . |

*Primary Examiner*—Gary Jackson
*Attorney, Agent, or Firm*—Wayne D. House

[57] ABSTRACT

A suture needle having, in sequence, a shaft portion, a tip portion, a conical point portion and a point. The shaft portion may be straight or curved, and cylindrical or tapered. The tip portion has at least two substantially flat surfaces. The conical point portion is of conical shape having a substantially round cross section adjacent to the point of the needle. A plane tangent to the surface of the conical point portion makes a greater angle with respect to the longitudinal centerline of the needle than does the angle formed by the intersection of a plane through a flat surface of the tip portion and the longitudinal centerline of the needle.

21 Claims, 5 Drawing Sheets

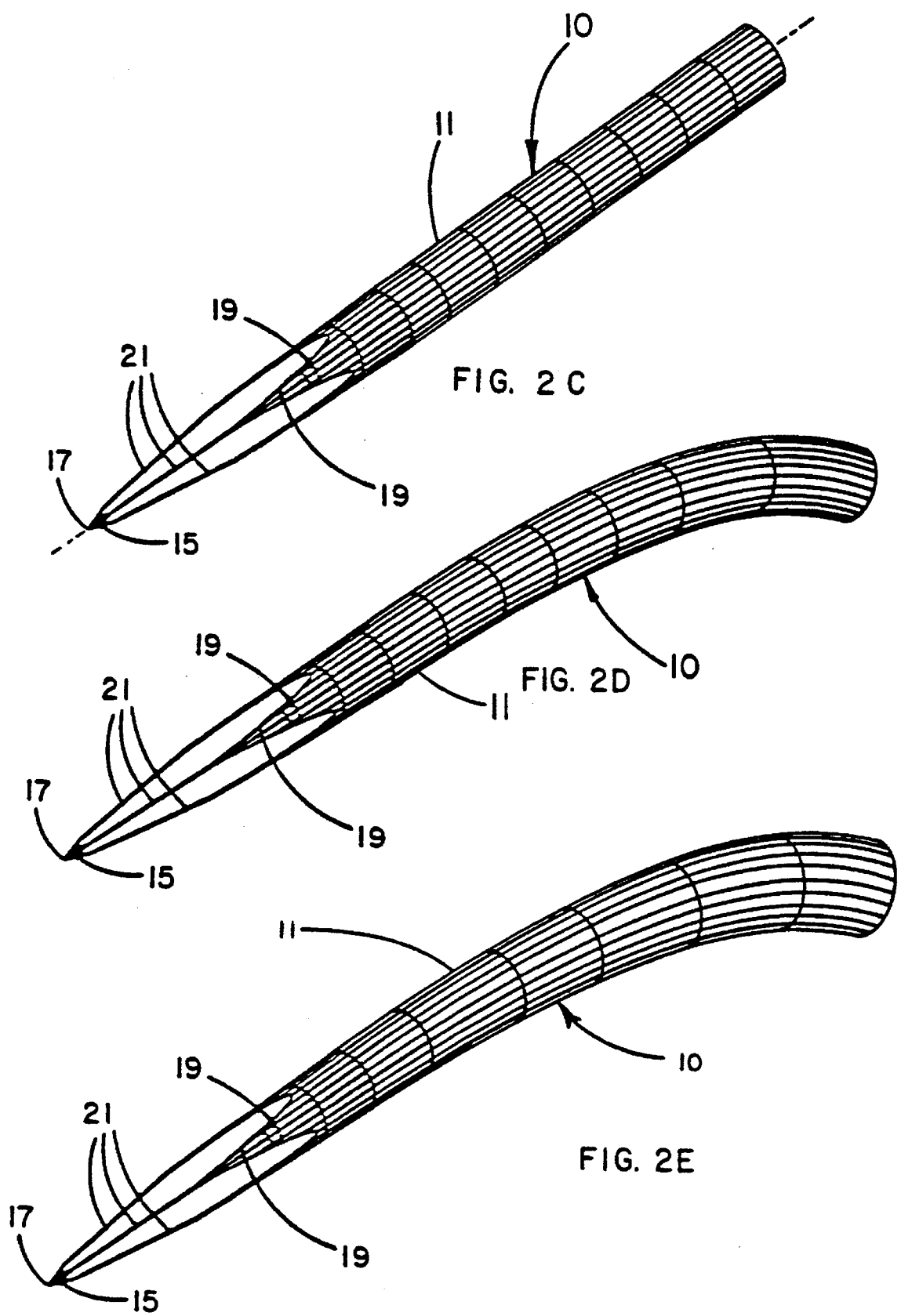

SUTURE NEEDLE

This application is a continuation of application Ser. No. 08/086,500 filed Jul. 1, 1993, now abandoned.

FIELD OF THE INVENTION

The present invention relates to the field of suture needles.

BACKGROUND OF THE INVENTION

Suture needles with cutting edges are conventionally made with tip portions having at least two substantially flat surfaces with a cutting edge disposed between the at least two flat surfaces. The flat surfaces are at a slight angle with respect to the longitudinal axis of the needle; these surfaces converge to form the point of the needle. A common problem with needles of this type is burring or bending of the point of the needle because of insufficient metal at the point to resist the stresses imposed on the point during use.

Additionally, if four or more flat surfaces are used to form the tip portion of the needle, it is quite difficult to manufacture the needle to repeatedly achieve a point resulting from a common, perfect intersection of the four or more flat surfaces with the longitudinal centerline of the needle.

U.S. Pat. No. 3,094,123 to Kurtz attempts to address these problems by removing the point of a cutting needle by grinding it away into an arc-like shape with the arc substantially perpendicularly intersecting the longitudinal centerline of the needle. This solution strengthens the tip of the needle but compromises the piercing effectiveness of the needle.

U.S. Pat. No. 3,636,955, also to Kurtz, proposes an alternative solution by describing a point formed by grinding away the needle tip to form a single planar surface that the inventor calls a chisel-type cutting edge. The planar surface is preferably 45° with respect to the longitudinal centerline of the needle. U.S. Pat. No. 4,128,351 also to Kurtz describes a similar solution. U.S. Pat. No. 4,513,747 to Smith proposes a similar solution wherein each flat surface of the tip portion is ground away at a greater angle with respect to the needle centerline than the angle formed by the remainder of the flat surface. This method thus requires an additional grinding step for each flat surface. If four flat surfaces are used, it does not avoid the manufacturing difficulty of achieving a common intersection point with the new tip surfaces.

SUMMARY OF THE INVENTION

The present invention is a surgical needle having, in sequence, a shaft portion, a tip portion, a conical point portion and a point. The needle has a longitudinal centerline. The shaft portion constitutes most of the length of the needle and is intended primarily to provide a useful gripping surface by which the needle may be grasped by a conventional needle driver. The shaft portion is typically of rounded cross section although other cross sections such as square or triangular are possible. The shaft portion may be cylindrical or tapered along its length, and may also be either straight or curved along its length wherein the longitudinal centerline is consequently also straight or curved. The tip portion comprises at least two flat surfaces and preferably has a cutting edge disposed between the flat surfaces. The tip portion may, for example, have as many as five flat surfaces and five cutting edges. Each flat surface lies in a plane that intersects the longitudinal centerline at a plane intersection angle. The conical point portion is of substantially round cross section adjacent to the point and forms a cone angle defined as the angle between a plane tangent to the surface of the conical point portion and the longitudinal centerline. The cone angle is greater than the plane intersection angle.

The conical point portion of the surgical needle of the present invention achieves a strong, burr-resistant point offering both good strength and good piercing characteristics with corresponding low penetration forces. The strength results from the cone angle being greater than the plane intersection angle, and also from the symmetric, round cross section of the conical point portion adjacent to the actual point. These two factors provide an increased cross sectional area adjacent to the point, thereby providing a substantial strength increase over conventional, prior art needles.

For a surgical needle where it is apparent that forces applied to the point may be from any direction, the use of a point having a symmetrical, round cross section provides for the greatest strength and resistance to burring or bending of the tip. Further, the conical point portion is simple to manufacture because of its symmetry. It may be made, for example, by grinding while rotating the needle with respect to the grinding surface. The conical point portion also reduces the need for four or more flat surfaces of the tip portion to be aligned to intersect at a common point.

The conical point portion may also be made to have a generally parabolic shape having a curved rather than straight profile.

The flat surfaces of the tip portion may also be made concave by the use of hollow grinding techniques. Flat surfaces herein include concave, hollow ground surfaces as well as truly flat surfaces. For purposes of calculating a plane intersection angle for these concave surfaces, the plane should intersect with the edges of the concave surface.

The use of a conical point portion also allows for the use of a smaller plane intersection angle, which in turn further reduces penetration forces during use.

A suture may be affixed to the end of the needle opposite the point by various methods known in the art.

BRIEF DESCRIPTION OF THE DRAWINGS

FIG. 2C is a perspective view of the needle of FIG. 2B having a substantially straight shaft portion rather than the tapered shaft portion of the needle of FIG. 2B.

FIG. 2D is a perspective view of the needle of FIG. 2C having a substantially curved shaft portion of constant diameter along its length in place of the substantially straight shaft portion of the needle of FIG. 2C.

FIG. 2E is a perspective view of the needle of FIG. 2C having a substantially curved shaft portion having a diameter that tapers along its length in place of the substantially straight shaft portion of the needle of FIG. 2C.

DETAILED DESCRIPTION OF THE INVENTION

Figure 1A:
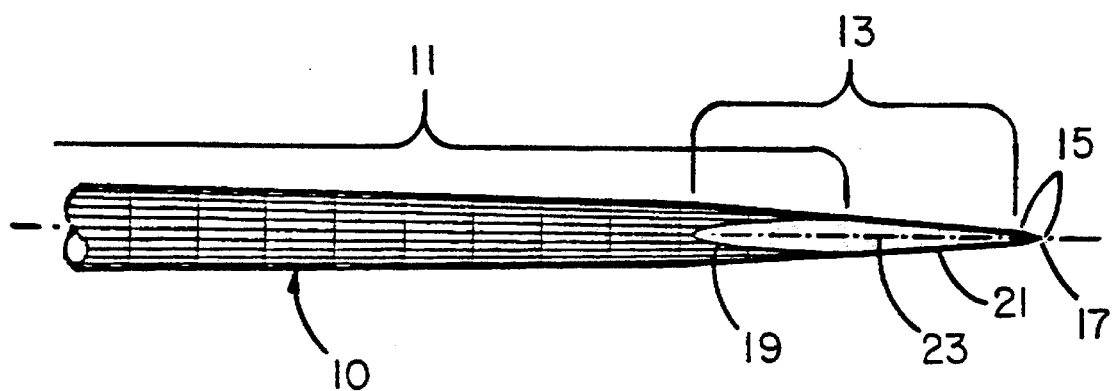
FIG. 1A describes a side or profile view of the suture needle of the present invention.

FIG. 1A describes a side view of the suture needle of the present invention. Needle 10 has a shaft portion 11, a tip portion 13, a conical point portion 15 and a point 17. Tip portion 13 comprises at least two flat surfaces 19. A cutting edge 21 may be disposed between the flat surfaces 19. Conical point portion 15 is of substantially round cross section adjacent to point 17. By substantially round cross section is meant a round or substantially rounded cross section without any sharp, angular or square edges. Substantially round cross sections include elliptical cross sections and sections incorporating straight edges connected by radiused edges such as the conical point portion 15 cross section of Figure 1B. FIG. 1C is a side view of the suture needle 10 that has been rotated 45° about the longitudinal centerline 23 with respect to the view of FIG. 1B.

The suture needle described in these figures has four flat surfaces 19 comprising the tip portion 13, wherein a cutting edge 21 may be disposed between each adjacent pair of flat surfaces 19. The use of four flat surfaces for the figures is descriptive only and is intended to represent all tip portion configurations having at least two flat surfaces, an optional cutting edge disposed between the two flat surfaces, a conical point portion and a point.

Figure 1B:
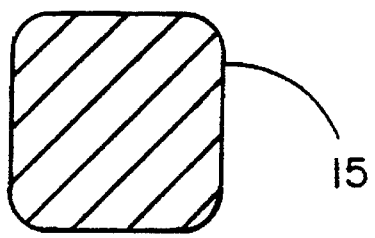
FIG. 1B describes a cross section of a conical point portion having a substantially rounded cross section.
Figure 1C:
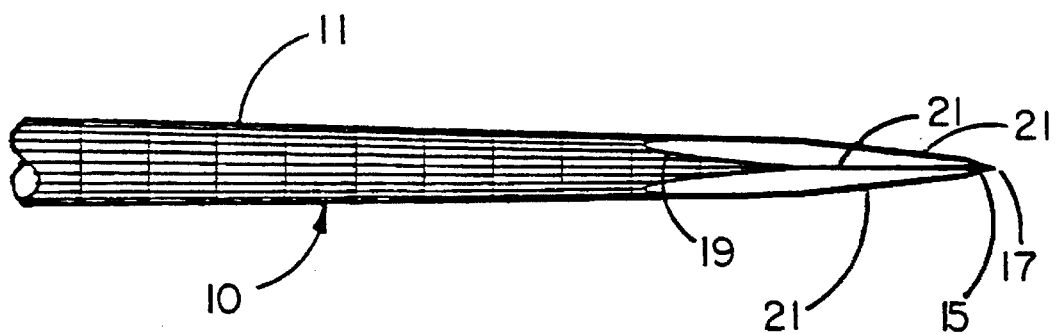
FIG. 1C is a side view of the suture needle that has been rotated 45° about the longitudinal centerline in comparison to the view of FIG. 1A.
Figure 2A:
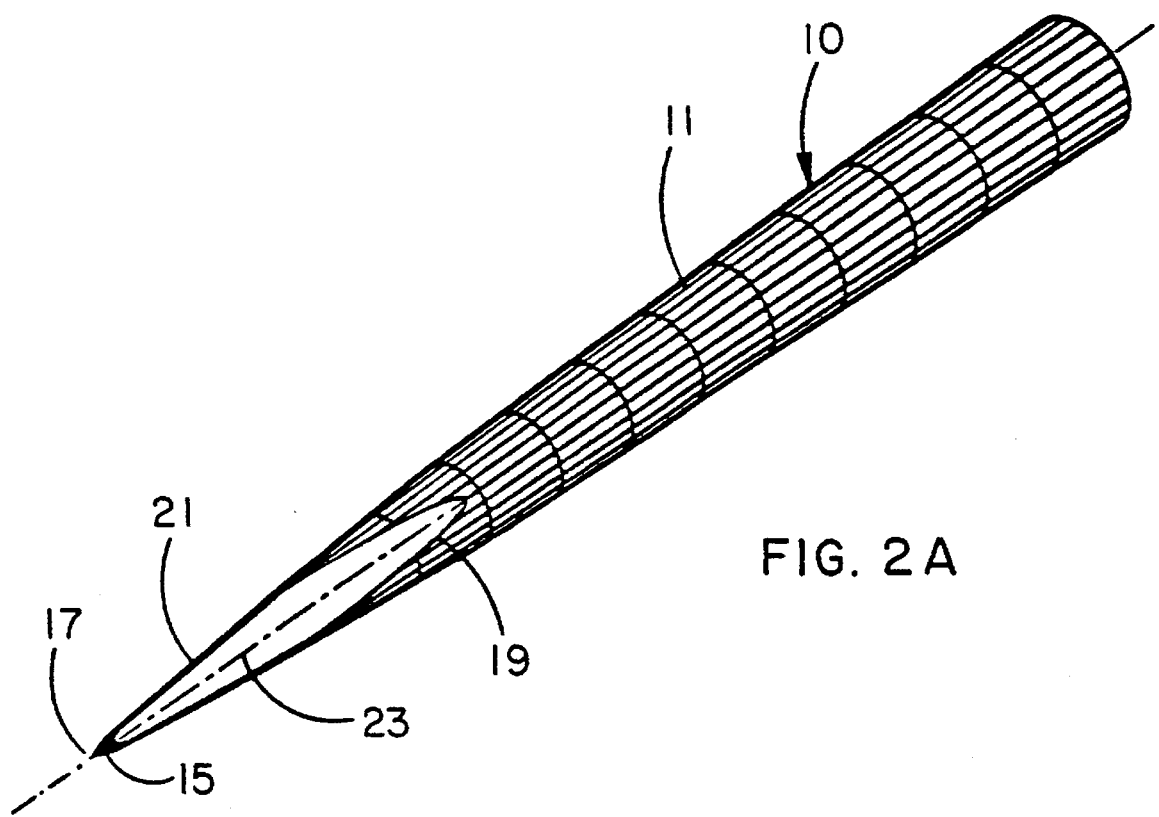
FIGS. 2A and 2B are perspective views of the side views presented by FIGS. 1A and 1C respectively.
Figure 2B:
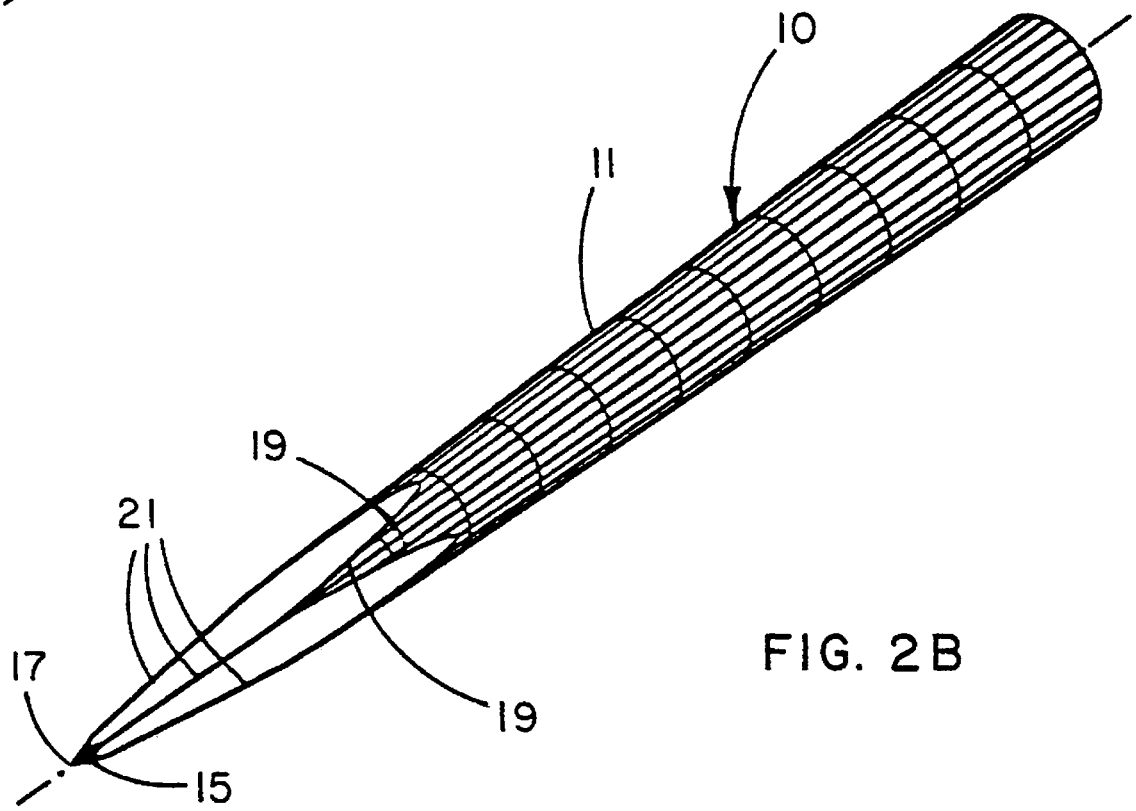

FIGS. 2A and 2B are perspective views of the side views presented by FIGS. 1A and 1B respectively. FIG. 2C is a perspective view of the needle of FIG. 2B having a substantially straight shaft portion rather than the tapered shaft portion of the needle of FIG. 2B. FIG. 2D is a perspective view of the needle of FIG. 2C having a substantially curved shaft portion of constant diameter along its length in place of the substantially straight shaft portion of the needle of FIG. 2C. FIG. 2E is a perspective view of the needle of FIG. 2C having a substantially curved shaft portion having a diameter that tapers along its length in place of the substantially straight shaft portion of the needle of FIG. 2C.

Figure 3:
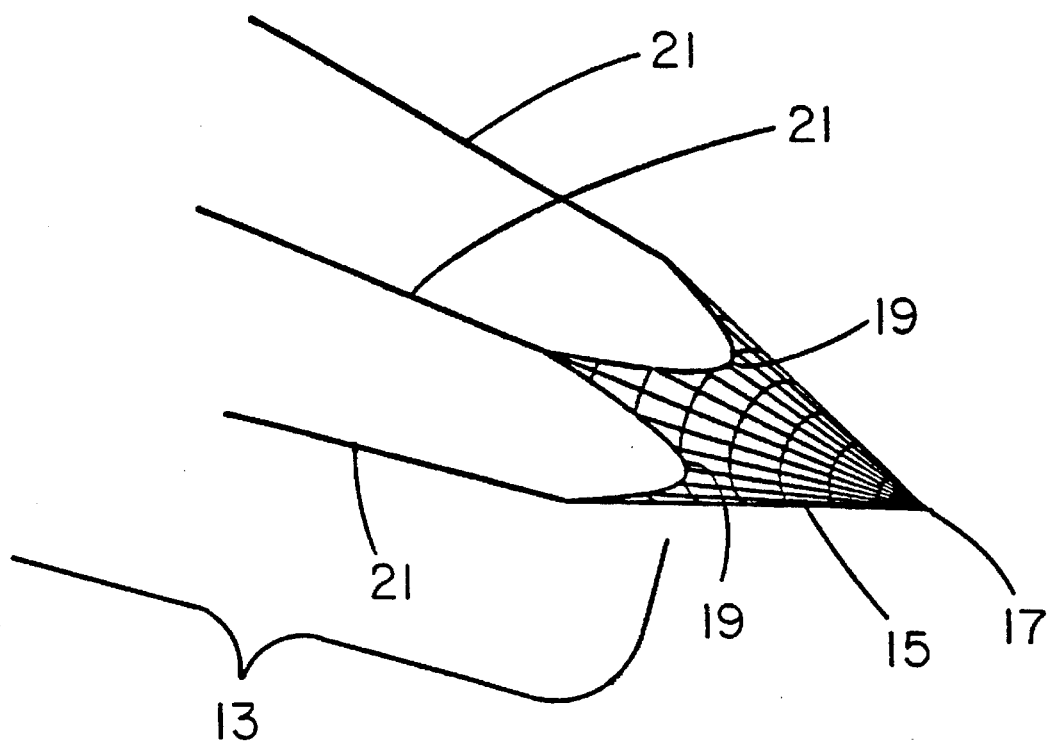
FIG. 3 describes a perspective close-up view of the conical point portion and adjacent tip portion of the surgical needle.
Figure 4:
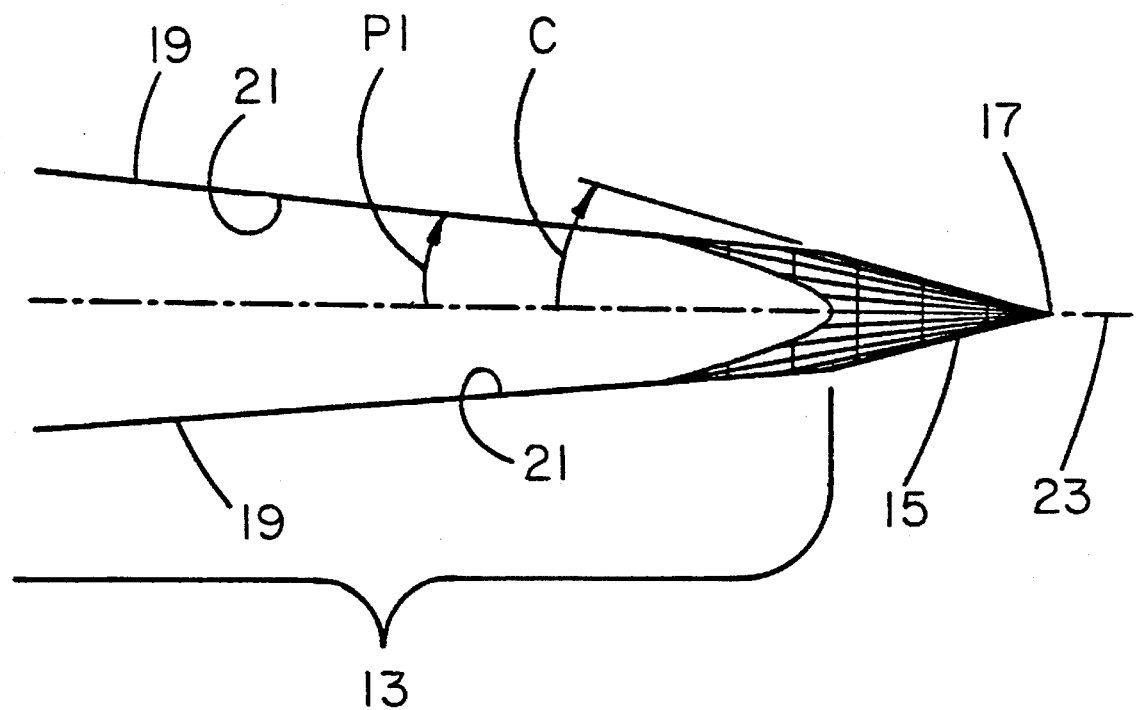
FIG. 4 is a side view that describes the angular relationship between the conical point portion and the flat surfaces of the tip portion.

FIG. 3 describes a perspective close-up view of the conical point portion 15 and adjacent tip portion 13 of the surgical needle. The corresponding side view of FIG. 4 describes cone angle C between a plane tangent to the surface of the conical point portion 15 and the longitudinal centerline 23, and plane intersection angle PI between the plane of a flat surface 21 and longitudinal centerline 23. It is apparent from FIGS. 3 and 4 that cone angle C is greater than plane intersection angle PI. These views also show how the use of conical point portion 15 allows the use of a smaller plane intersection angle PI than would otherwise be practical because the point would be extremely weak with such a small plane intersection angle if a separate conical point portion was not used.

Figure 5:
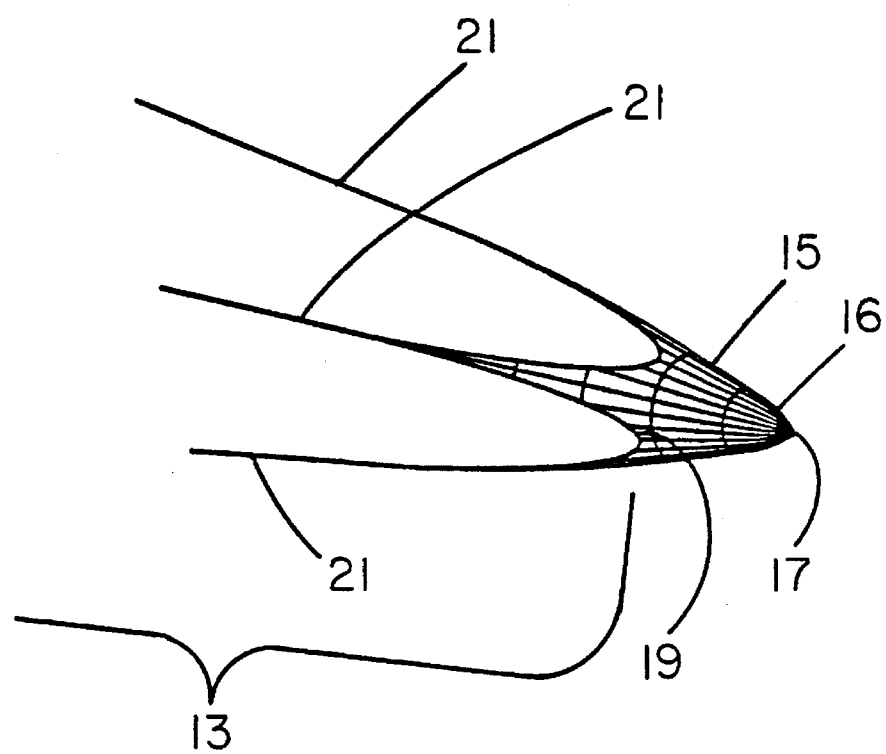
FIG. 5 describes a perspective view of a conical point portion having a generally parabolic shape.
Figure 6:
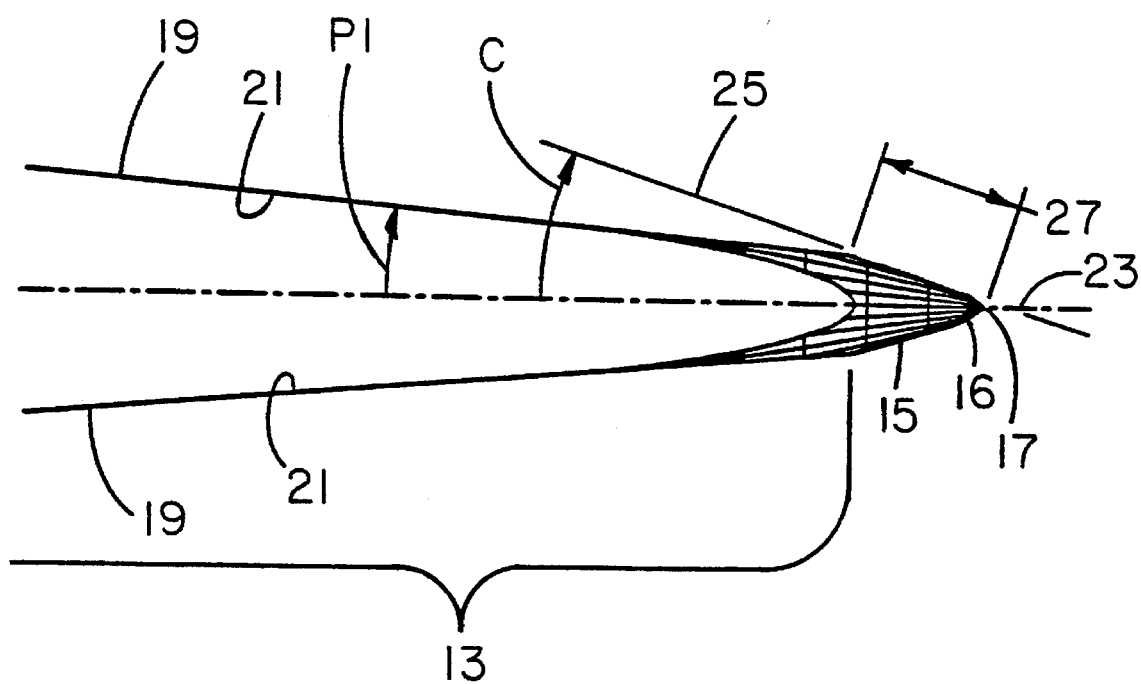
FIG. 6 is a side or profile view of a conical point portion having a generally parabolic shape and showing the angular relationship between the conical point portion and the flat surfaces of the tip portion.

The conical point portion 15 may be of a generally parabolic shape having a curved profile 16 as shown by the perspective view of FIG. 5. Such a curved profile is of a substantially round cross section adjacent to the point. For purposes of determining cone angle C for these parabolic shapes, the plane 25 tangent to the conical point portion 15 is to be fitted tangent to the conical point portion at the midpoint of the length 27 of the conical point portion 15. This is described by FIG. 6. The length 27 of the conical point portion 15 is defined as the shortest distance between the point 17 and the intersection of the conical point portion 15 and the flat surface 19.

We claim:

1. A suture needle comprising, in sequence, a shaft portion, a tip portion, a conical point portion and a point, and further having a longitudinal centerline, wherein the tip portion has at least two flat surfaces, said flat surfaces each being in a plane that intersects the centerline at a plane intersection angle, and further having a conical point portion of substantially round cross section, wherein said conical point portion has a surface and said conical point portion forms a cone angle between a plane tangent to the surface of the conical point portion and the longitudinal centerline, and wherein said cone angle is greater than said plane intersection angle.

2. A suture needle according to claim 1 wherein the shaft portion is a cylindrical shaft portion of substantially constant diameter along the length of the shaft portion.

3. A suture needle according to claim 2 wherein the tip portion has two flat surfaces.

4. A suture needle according to claim 2 wherein the tip portion has three flat surfaces.

5. A suture needle according to claim 2 wherein the tip portion has four flat surfaces.

6. A suture needle according to claim 2 wherein the tip portion has five flat surfaces.

7. A suture needle according to claim 1 wherein the shaft portion is a tapered shaft portion of varying diameter along the length of the shaft portion.

8. A suture needle according to claim 7 wherein the tip portion has two flat surfaces.

9. A suture needle according to claim 7 wherein the tip portion has three flat surfaces.

10. A suture needle according to claim 7 wherein the tip portion has four flat surfaces.

11. A suture needle according to claim 7 where n the tip portion has five flat surfaces.

12. A suture needle according to claim 1 wherein the shaft portion is substantially straight along the length of the shaft portion.

13. A suture needle according to claim 12 wherein the tip portion has two flat surfaces.

14. A suture needle according to claim 12 wherein the tip portion has three flat surfaces.

15. A suture needle according to claim 12 wherein the tip portion has four flat surfaces.

16. A suture needle according to claim 12 wherein the tip portion has five flat surfaces.

17. A suture needle according to claim 1 wherein the shaft portion is substantially curved along the length of the shaft portion.

18. A suture needle according to claim 17 wherein the tip portion has two flat surfaces.

19. A suture needle according to claim 17 wherein the tip portion has three flat surfaces.

20. A suture needle according to claim 17 wherein the tip portion has four flat surfaces.

21. A suture needle according to claim 17 wherein the tip portion has five flat surfaces.

* * * * *